(12) United States Patent
Meier

(10) Patent No.: US 9,050,134 B2
(45) Date of Patent: Jun. 9, 2015

(54) DEVICE AND METHOD FOR VERIFYING COMPATABILITY BETWEEN COOPERATING PARTS OF A JOINT PROSTHESIS

(71) Applicant: Zimmer GmbH, Winterthur (CH)

(72) Inventor: Rolf Meier, Winterthur (CH)

(73) Assignee: Zimmer GmbH, Winterthur (CH)

( * ) Notice: Subject to any disclaimer, the term of this patent is extended or adjusted under 35 U.S.C. 154(b) by 296 days.

(21) Appl. No.: 13/799,376

(22) Filed: Mar. 13, 2013

(65) Prior Publication Data
US 2014/0155945 A1    Jun. 5, 2014

(30) Foreign Application Priority Data
Nov. 30, 2012    (EP) ..................... 12194938

(51) Int. Cl.
| | |
|---|---|
| *A61B 17/56* | (2006.01) |
| *A61F 2/32* | (2006.01) |
| *A61B 19/00* | (2006.01) |
| *A61F 2/46* | (2006.01) |
| *A61F 2/30* | (2006.01) |

(52) U.S. Cl.
CPC ............... *A61B 17/56* (2013.01); *A61F 2/4657* (2013.01); *A61B 19/50* (2013.01); *A61F 2/32* (2013.01); *A61F 2002/30532* (2013.01); *A61B 2019/502* (2013.01)

(58) Field of Classification Search
CPC ........ A61B 17/56; A61B 19/46; A61B 19/50; A61B 2017/564; A61B 2019/461; A61B 2019/467; A61B 2019/502; A61B 2019/508; A61F 2/32; A61F 2/4657; A61F 2002/30532
USPC ...................... 33/512, 562; 606/102; 623/912
See application file for complete search history.

(56) References Cited

U.S. PATENT DOCUMENTS

| | | | |
|---|---|---|---|
| 5,342,366 A | 8/1994 | Whiteside et al. | |
| 6,799,380 B2 * | 10/2004 | Afriat | ............................. 33/562 |
| 7,388,972 B2 * | 6/2008 | Kitson | .......................... 382/128 |
| 8,533,968 B2 * | 9/2013 | Anapliotis et al. | .............. 33/512 |
| 8,858,469 B2 * | 10/2014 | Brooks et al. | ................. 600/587 |
| 2010/0106253 A1 | 4/2010 | Brooks | |
| 2011/0166666 A1 * | 7/2011 | Meulink et al. | ............ 623/22.42 |
| 2011/0247229 A1 | 10/2011 | Anapliotis et al. | |

FOREIGN PATENT DOCUMENTS

WO    WO-2008132424 A1    11/2008

OTHER PUBLICATIONS

"European Application Serial No. 13194548.7, Extended European Search Report mailed Mar. 12, 2014", 6 pgs.

* cited by examiner

*Primary Examiner* — R. A. Smith
(74) *Attorney, Agent, or Firm* — Schwegman Lundberg & Woessner, P.A.

(57) ABSTRACT

The present disclosure relates to devices and methods for verifying compatibility between cooperating parts of a joint prosthesis. The compatibility between the cooperating parts is with respect to at least one articulation parameter.

20 Claims, 3 Drawing Sheets

DEVICE AND METHOD FOR VERIFYING COMPATABILITY BETWEEN COOPERATING PARTS OF A JOINT PROSTHESIS

RELATED APPLICATIONS

This patent document is related to, and claims the benefit of priority of, European Patent Application No. EP 12194938.2, filed on Nov. 30, 2012, the entirety of the disclosure of which is explicitly incorporated by reference herein.

BACKGROUND

The present disclosure relates to devices and methods for verifying compatibility between cooperating parts of a joint prosthesis.

Joint prostheses, such as artificial hip joints, comprise two cooperating parts that, in the implanted state, articulate with respect to each other. In an artificial hip joint, an acetabular shell and a femoral head, which is fixed to a femoral stem, articulate with respect to each other. In other words, during articulation, the stem cooperates with the shell via the head. As described herein, when referring to an artificial hip joint, the shell and the corresponding femoral head can be regarded as a first one of the cooperating parts, while the stem can be regarded as a second one of the cooperating parts.

Usually, manufacturers of joint prostheses provide their customers with a complete prostheses, i.e., with both cooperating parts. Before this background, there has been no need for a surgeon to verify whether the two cooperating parts are actually compatible with each other. Specifically, the surgeon can be sure that the two parts fulfill all relevant requirements for the articulation, which is to be provided by the two parts in the implanted state.

In hip replacement surgery, for example, it is known for the skilled person that the so-called range of motion ("ROM") is an important articulation parameter. Artificial hip joints have to meet minimum ROM requirements, which are, for example, defined by an international standard (e.g., ISO 21535). These requirements comprise minimum articulation angles in specific planes, for example the anterior/posterior plane ("A/P plane") and the medial/lateral plane ("M/L plane"), as further explained below.

As mentioned above, for a joint prosthesis that is provided completely from one single manufacturer, there is no need for the surgeon to verify whether or not the two articulating or cooperating parts of the prosthesis actually meet these ROM requirements since the manufacturer guarantees that this is the case.

However, when the first part of a joint prosthesis is provided by a first manufacturer and the second part of the prosthesis is provided by a second, different manufacturer, the surgeon has to make sure that these two parts are compatible with each other with regard to all relevant parameters, specifically with regard to one or more articulation parameters such as minimum articulation angles for the ROM.

In hip replacement surgery, for example, the minimum ROM requirements require a verification of the compatibility in both the A/P plane and the M/L plane. As known to the skilled person, the A/P plane is perpendicular to an A/P axis extending in anterior-posterior direction, while the M/L plane is a plane perpendicular to an M/L axis extending in medial/lateral direction.

Generally, all anatomical terms as mentioned in the present disclosure and relating to directions or locations, such as anterior, posterior, medial, lateral, proximal and distal, refer to an implanted state of the respective parts and implants described herein.

OVERVIEW

Before the above-explained background, one object of the present disclosure is to provide a device and a method for verifying compatibility between cooperating parts of a joint prosthesis with respect to at least one articulation parameter. In another object of the invention, a device and method are provided to enable a surgeon to assess whether prosthetic parts from different manufacturers can be used as cooperating parts of a joint prosthesis. Specifically, in one embodiment, the object of this disclosure is to enable a surgeon to verify, in one or both of the A/P plane and the M/L plane, whether or not a particular stem from a manufacturer (a second manufacturer) fulfills the respective minimum ROM requirements if used with an acetabular shell and femoral head arrangement from another manufacturer (a first manufacturer), for example his/her preferred or standard manufacturer, to form a hip joint prosthesis.

The present disclosure provides such devices and methods as defined in the independent claims. Embodiments of these devices and methods are defined in the dependent claims. Generally, the present disclosure relates to the provision and use of one or more templates (referred to herein as "reference templates") allowing a surgeon, by easy-to-perform visual inspection, to assess compatibility of a first part (e.g., an acetabular shell/femoral head arrangement) with a second part (e.g., a femoral stem) of a joint prosthesis (e.g., a hip joint prosthesis). The reference templates represent specific information about the two parts of the prospective joint prosthesis, and about requirements for the joint articulation (e.g., minimum articulation angles for the range of motion in the A/P plane and in the M/L plane), which the two parts have to fulfill if used together as the joint prosthesis.

Generally, the reference template represents certain maximum allowable dimensions of a second part in a particular plane (e.g., A/P plane or M/L plane), so that every second part that lies within these plane dimensions is allowed, i.e., is considered compatible with the first part and may thus be used together with the first part in a joint prosthesis.

In an embodiment, a first reference template for the A/P plane and a second reference template for the M/L plane are provided.

In another embodiment, the reference template has been obtained on the basis of an acetabular shell/femoral head arrangement from a first manufacturer. In further embodiments, the reference template is obtained on the basis of constraints relating to a femoral stem from a particular manufacturer and to minimum articulation angles for the ROM in the A/P plane and for the ROM in the M/L plane. Femoral stem constraints may include, for example, stem neck diameter, geometry, length and taper length, and proximal stem geometry.

In some embodiments, the reference template includes certain boundaries or a periphery of at least a portion of a stem obtained on the basis of a virtual stem. This virtual stem represents specific desired or required ranges, maximum values and/or minimum values for specific geometrical properties of an actual stem desired for use with a select acetabular shell/femoral head arrangement in a joint prosthesis. For example, but not by way of limitation, the virtual stem may have a maximum allowed neck diameter so that any actual stem having a neck diameter equal to or smaller than the neck diameter of the virtual stem will lie within the stem neck boundaries provided by the reference template. In other words, all actual stems that lie within geometric boundaries or periphery of the virtual stem reference template—when properly aligned with the reference template—fulfill the minimum ROM requirements.

For a particular verification plane (e.g., A/P plane or M/L plane), a reference template enables the surgeon to distinguish between actual stems that are allowed or compatible with a select acetabular shell/femoral head arrangement, and actual stems that are not allowed or that are not compatible with the select acetabular shell/femoral head arrangement, in an easy and reliable manner by visual inspection.

In one embodiment, the boundaries of the first reference template represent, at least in part, a projection of the properly aligned virtual stem into the first verification plane.

The actual stems to be verified are in each case represented by a prosthetic component (e.g., stem) template, which is provided by the manufacturer. The manufacturer provided templates (referred to herein as "prosthetic templates") are typically used to determine the appropriate prosthetic dimensions (e.g., stem dimensions) for a particular patient. The prosthetic templates may be provided in different sizes corresponding to a variety of x-ray magnifications (e.g., 15%, 20%, etc.) that may be used to image the patient's joint.

Since the prosthetic templates are provided in various magnifications, the reference templates of the present disclosure are also provided in a variety of sizes or "magnifications" to correspond to prosthetic template magnifications. To verify whether an actual stem is compatible with a select acetabular shell/femoral head arrangement, the surgeon will select a reference template of a "magnification" or enlargement comparable to the magnification or enlargement of the prosthetic template for which verification of compatibility is desired.

The virtual stem, which corresponds to the boundaries of the reference template, may represent further preferred geometrical properties of actual stems such as the design of the fixation taper of the stem, the caput-collum-diaphyseal ("CCD") angle of the stem and the offset of the femoral head.

In another embodiment, there is provided a verification method in which reference template for a select acetabular shell/femoral head arrangement is aligned with the prosthetic template of stem by superimposing one of the reference template or the prosthetic template over the other one of the templates, aligning the templates. In another embodiment, the method includes aligning the reference template and the prosthetic template along an alignment reference of which comprises an articulation center (center of the prospective femoral head) and a straight alignment axis (e.g., through the center line or neck axis of the stem of each one of the reference template and the prosthetic template.

To better illustrate the device and related and methods disclosed herein, a non-limiting list of embodiments is provided here:

In Embodiment 1, a method for verifying compatibility between a first part and a second part of a joint prosthesis, with respect to at least one articulation parameter, comprises: providing or receiving at least one two-dimensional reference template defining at least one verification plane and obtained on a basis of the first part, one or more constraints relating to the second part, and the at least one articulation parameter, the reference template comprising an alignment reference and one or more boundaries; providing or receiving a two-dimensional prosthesis template corresponding to a shape of the second part, as viewed in the at least one verification plane; aligning the prosthesis template with the at least one reference template by superimposing the two templates and aligning the prosthesis template to the reference template using the alignment reference; and considering the second part as compatible with the first part if the shape of the second part lies within the one or more boundaries of the at least one reference template, when the at least one reference template and the prosthesis template are aligned.

In Embodiment 2, the method of Embodiment 1 is optionally modified such that the one or more boundaries of the reference template are obtained on the basis of a virtual second part having at least one predetermined geometrical property and fulfilling at least one predefined requirement for the articulation parameter for which the geometrical property is critical, including wherein the one or more boundaries of the reference template are obtained, at least in part, by a projection of the virtual second part into the at least one verification plane.

In Embodiment 3, the method of Embodiment 2 is optionally modified such that the predetermined geometrical property of the second part is one of a diameter of the neck of a femoral stem, a fixation taper of the femoral stem, a CCD angle of the femoral stem, or an offset of a femoral head.

In Embodiment 4, the method of Embodiment 2 is optionally modified such that the predefined requirement for the articulation parameter is a minimum articulation angle for a range of motion.

In Embodiment 5, the method of any one or any combination of Embodiments 1-4 is optionally modified such that the first part comprises an acetabular shell and a femoral head arrangement, the second part comprises a femoral stem to be fixed to the femoral head, and the articulation parameter comprises a range of motion with respect to articulation about at least one axis.

In Embodiment 6, the method of Embodiment 5 is optionally modified such that the at least one axis comprises one of a first axis extending in an anterior-posterior direction or a second axis extending in a medial-lateral direction.

In Embodiment 7, the method of any one or any combination of Embodiments 1-6 is optionally modified such that the alignment reference comprises an articulation center and a straight alignment axis.

In Embodiment 8, the method of any one or any combination of Embodiments 1-7 is optionally modified such that the alignment reference comprises a head center of a femoral stem and a center line or neck axis of the femoral stem.

In Embodiment 9, the method of any one or any combination of Embodiments 1-8 is optionally modified such that the at least one reference template comprises a first and a second reference template, the at least one verification plane comprises a first and a second verification plane defining verification planes for, respectively, the first and second reference templates.

In Embodiment 10, the method of Embodiment 9 is optionally modified such that the first verification plane is perpendicular to an anterior-posterior direction and the second verification plane is perpendicular to a medial-lateral direction.

In Embodiment 11, a device for verifying compatibility between a first part and a second part of a joint prosthesis, comprises: at least one two-dimensional reference template defining at least one verification plane and obtained on a basis of the first part, constraints relating to the second part, and the articulation parameter, the at least one reference template comprising a boundary and an alignment reference configured to align the at least one reference template with a two-dimensional prosthesis template having a shape of the second part, as viewed in the at least one verification plane.

In Embodiment 12, the device of Embodiment 11 is optionally configured such that the boundaries of the at least one reference template are obtained on the basis of a virtual second part having at least one predetermined geometrical property and fulfilling at least one predefined requirement for the articulation parameter for which the geometrical property is critical.

In Embodiment 13, the device of any one or any combination of Embodiments 11 or 12 is optionally configured such that the alignment reference comprises an articulation center and a straight alignment axis.

In Embodiment 14, the device of any one or any combination of Embodiments 11-13 is optionally configured such that the first part comprises an acetabular shell and a femoral head arrangement, the second part comprises a femoral stem to be fixed to the femoral head, and the alignment reference comprises a head center of the femoral stem and a center line or neck axis of the femoral stem.

In Embodiment 15, the device of any one or any combination of Embodiments 11-14 is optionally configured such that the at least one reference template comprises a plurality of reference templates, each one of the plurality of reference templates represents a second part shape of a different size or scale.

In Embodiment 16, the device of Embodiment 15 is optionally configured such that the scale is between 115% and 120% of an anatomical size of the first part.

In Embodiment 17, the device of any one or any combination of Embodiments 11-16 optionally comprises a thin physical carrier, a transparency, or a piece of paper configured to receive and carry a marking or indicia, wherein the at least one reference template comprises the marking or indicia.

In Embodiment 18, the device of any one or any combination of Embodiments 11-17 optionally comprises a computer system, including a visual display, and wherein the at least one reference template is adapted to be viewed on the display.

In Embodiment 19, a method for producing a device for verifying compatibility between a first part and a second part of a joint prosthesis, with respect to at least one articulation parameter, comprises: providing or obtaining a two-dimensional reference template defining a verification plane, the reference template obtained on a basis of the first part, constraints relating to the second part, and to the articulation parameter; and providing or obtaining the reference template with one or more reference boundaries and an alignment reference for aligning the reference template with a two-dimensional prosthesis template having the shape of the second part as viewed in the first verification plane.

In Embodiment 20, the method of Embodiment 19 is optionally modified such that the one or more boundaries of the reference template are obtained on the basis of a virtual second part having at least one predetermined geometrical property and fulfilling at least one predefined requirement for the articulation parameter for which the geometrical property is critical.

In Embodiment 21, the device and related kits and methods of any one (or portion of any one) or any combination of Embodiments 1-20 is optionally configured such that all elements or options recited are available to use or select from.

These and other examples and features of the present devices and methods will be set forth in part in the following Detailed Description, drawings and claims. This Overview is intended to provide non-limiting examples of the present subject matter—it is not intended to provide an exclusive or exhaustive explanation. The Detailed Description below is included to provide further information about the present devices and related methods.

DETAILED DESCRIPTION

Figure 1A:
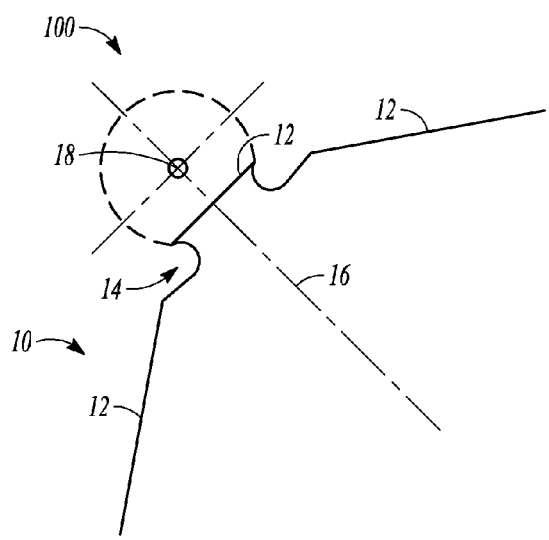
FIG. 1a illustrates a schematic view of a reference template of the present invention for verifying compatibility in the A/P plane.

In the following, the present disclosure will be explained with respect to embodiments and with reference to the accompanying drawings. In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present patent document.

Figure 1B:
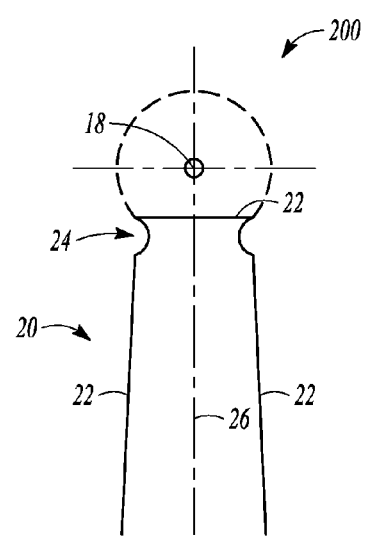
FIG. 1b illustrates a schematic view of a reference template of the present invention for verifying compatibility in the M/L plane.

FIG. 1a illustrates an embodiment of an A/P reference template 100 for determining whether a prospective prosthesis component (hereinafter, a "second prosthetic part") is compatible with a select acetabular shell/femoral head arrangement (sometimes referred to herein as a "first prosthetic part") in the A/P plane 10. FIG. 1b illustrates an embodiment of a reference template 200 for validation of a prospective second prosthetic part in the M/L plane 20.

In an embodiment shown in FIG. 1a, the A/P reference template 100 comprises a graphical representation of the periphery, boundaries or border lines 12 of at least a portion of a virtual second prosthetic part in the A/P plane 10. In another embodiment (FIG. 1b), the M/L reference template 200 comprises a graphical representation of the periphery, boundaries or border lines 22 of at least a part of a virtual second prosthetic part (e.g., a femoral stem) in the M/L plane 20.

The reference template 100, 200 may further comprise an alignment reference for aligning a prosthetic template 40, 50 (as shown in FIGS. 2-5) with the reference template 100, 200. For example, in one embodiment, the alignment reference may include indicia for referencing the position of a femoral head center 18. In an alternate embodiment, the alignment reference may comprise indicia referencing a straight, longitudinal alignment axis 16, 26 corresponding to the longitudinal axis through the center of the neck 14, 24 of the virtual femoral stem represented in the respective A/P and M/L reference template 100, 200. In FIGS. 1a and 1b, a virtual femoral head is depicted in broken lines for illustration of the alignment reference. The virtual femoral head illustrated in FIGS. 1a and 1b (area bordered by the broken lines) is not part of the reference template, which is shown in FIGS. 2 to 5 without a virtual femoral head.

The A/P reference template 100 and the M/L reference template 200 are provided on a physical carrier (not shown). The reference templates of the present disclosure may be in the form of a thin physical carrier such as a transparency or a piece of paper, sheet, transparency, film, board or other material suitable for receiving and displaying an imprint, image or other indicia representing the boundaries 12, 22 and the alignment reference 18, 16, 26. In alternate embodiments, the reference carrier of the present disclosure may comprise a computer screen or monitor, digital display or other device used in connection with a stationary or mobile computer system for viewing an embodiment of the reference template provided as a graphical display of digital or electronic data. The digital reference templates 100, 200 may be provided as two-dimensional templates or as three-dimensional templates.

The carrier, when imprinted with or displaying an embodiment of the reference template 100, 200 of the invention, may be referred herein to as a "reference carrier." The A/P reference template 100 and the M/L reference template 200 may be provided in the same carrier or in separate carriers, or electronic or digital versions of the reference templates 100, 200 may be viewed in the same reference carrier screen or display or on different reference carrier screens or displays. In certain embodiments, at least a portion of the carrier is transparent, translucent, semi-transparent or semi-translucent, to facilitate the determination of prosthetic component compatibility.

Figure 1C:
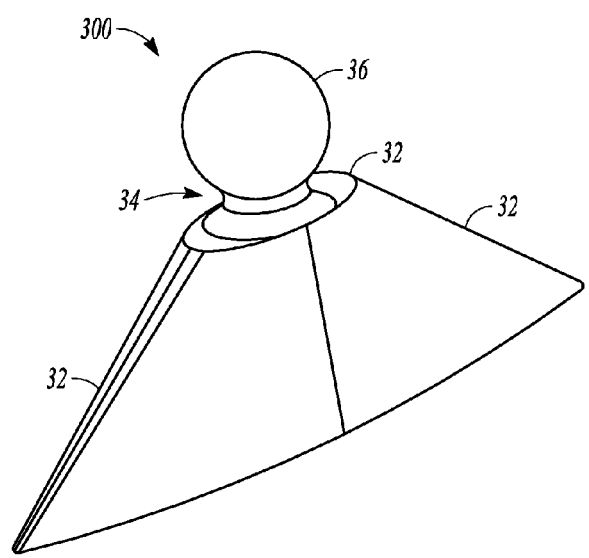
FIG. 1c illustrates an isometric view of a virtual stem.

As already mentioned before, the boundaries 12, 22 of the reference templates 100, 200 represent information based on a given acetabular shell/femoral head arrangement and on a virtual stem 300 (shown with the femoral head in FIG. 1c). Each acetabular shell/femoral head arrangement will have a reference template 100, 200, respectively, in each of the A/P plane and the M/L plane that is based upon a virtual stem 300 specific for that particular acetabular shell/femoral head arrangement.

A virtual stem 300 for a particular acetabular shell/femoral head arrangement may include a head portion 36, a neck portion 34 and stem boundaries 32.

The boundaries 12, 22 of the reference templates 100, 200 are provided such that, in the respective A/P plane 10 or M/L plane 20, every actual femoral stem that is allowable or compatible with the select acetabular shell/femoral head arrangement is smaller than the virtual stem 300 (FIG. 1c), lies within the boundaries of the reference template 100, 200, and thus meets the minimum ROM requirement, enabling articulation of the prospective joint prosthesis through the minimum articulation angle. In other words, each actual stem, if viewed in the respective A/P plane 10 or M/L plan 20, which lies within the respective reference template boundaries 12, 22 is able to articulate through the required minimum articulation angle without impingement and without mechanical abutment between the stem and the acetabular shell selected for the joint prosthesis.

The embodiments of the reference templates 100, 200 may be used to determine whether a particular femoral stem from a manufacturer can be used with a select acetabular shell/femoral head arrangement from a different manufacturer. In an embodiment of the method, the surgeon first selects or receives an acetabular shell and a femoral head to be used in the first prosthetic part of the joint prosthesis. Next, the surgeon selects or receives a femoral stem to be assessed for compatibility with the selected acetabular shell/femoral head arrangement. The surgeon selects or receives a prosthesis template 40, 50 (shown in FIGS. 2-5) from the femoral stem manufacturer. The prosthesis template corresponds to the select femoral stem. The prosthesis template 40, 50 is preferably selected in a size or magnification to match the patient x-ray image size or magnification, or is otherwise selected according to the size templating procedure established by the manufacturer of the select femoral stem. The prosthesis template 40, 50 includes alignment references, such as a head center 42, 52 and a longitudinal alignment axis 44, 54. The alignment references may be indicated as a perforations, other markings or indicia on the prosthesis template 40, 50. In certain embodiments, the reference templates 100, 200 are adapted to be used with femoral stem sizing templates of actual femoral stems having a CCD angle between 115° and 150°. Possible diameters of the femoral head are, for example, 28 mm, 32 mm, 36 mm or 40 mm.

As already mentioned above, the reference templates 100, 200 of the present disclosure are available in a variety of sizes to correspond to a variety of x-ray magnifications, for example, 15% magnification and 20% magnification. The surgeon selects a reference carrier having a reference template 100, 200 for the selected acetabular shell/femoral head arrangement. Preferably, the reference template has a size corresponding to the magnification or size of the selected prosthesis template 40, 50.

Figure 2:
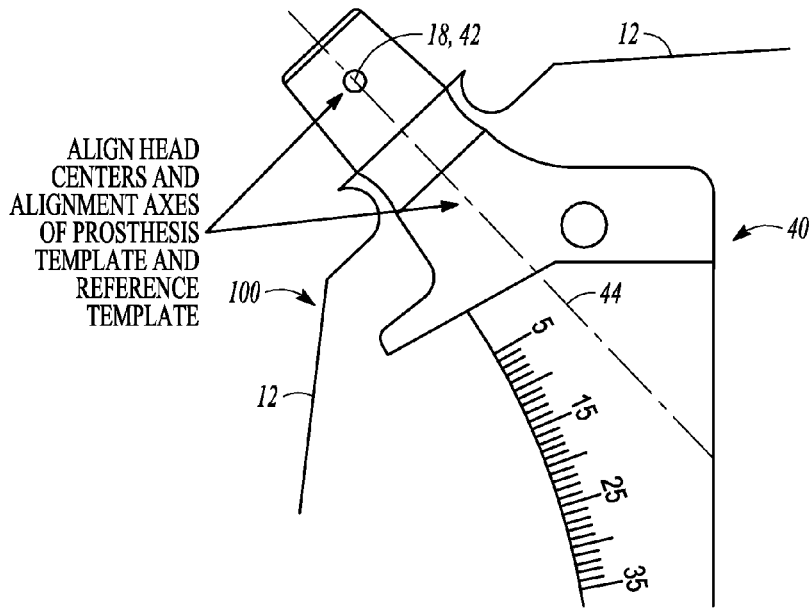
FIG. 2 illustrates a reference template of the present invention aligned with a prosthetic template in the A/P plane.
Figure 3:
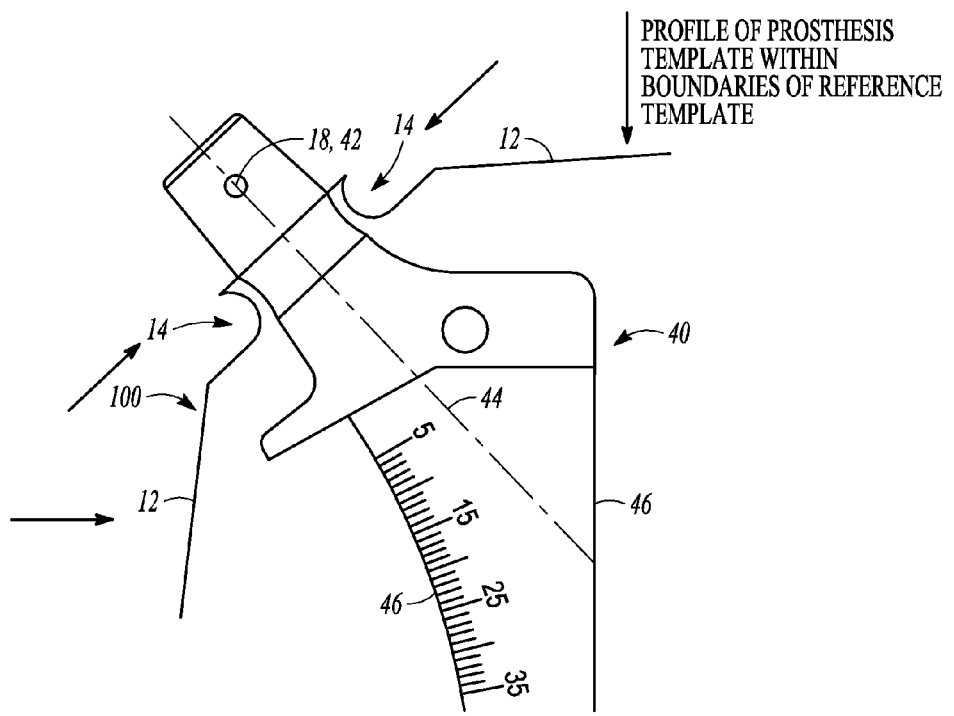
FIG. 3 illustrates visual inspection of the reference template of the present invention aligned with a prosthetic template in the A/P plane according to FIG. 2.
Figure 4:
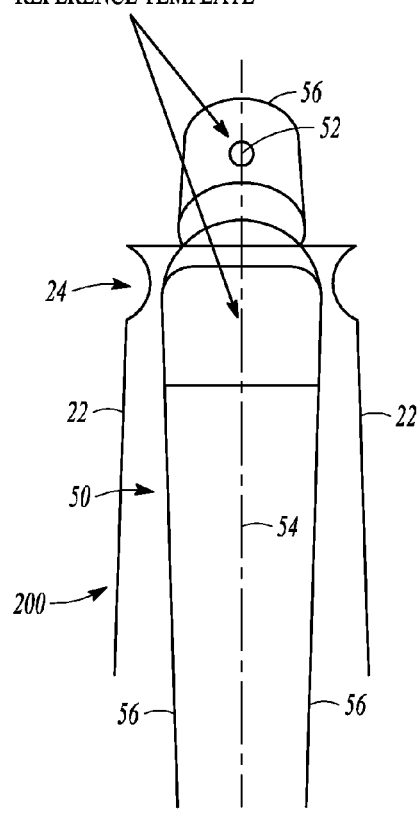
FIG. 4 illustrates a reference template of the present invention aligned with a prosthetic template in the M/L plane.

As shown in FIGS. 2-5, the surgeon next determines whether the select femoral stem is compatible in each one of the A/P plane 10 and M/L plane 20. The order of determination is not significant, and the surgeon may first determine compatibility in the A/P plane and then in the M/L plane, or may first assess compatibility in the M/L plane and then in the A/P plane. To determine compatibility in a particular plane, the respective reference template (A/P plane reference template 100 or M/L plane reference template 200) is placed or displayed over a background that permits the reference template 100, 200 to be visible, for example a white or other light-colored background. Preferably the background is a smooth, flat surface. As shown in FIGS. 2 and 3, in the A/P view (corresponding to the A/P plane 10) the manufacturer's prosthetic template 40 is superimposed over an embodiment of the A/P reference template 100. In an aligning step (shown in FIG. 2) for determining compatibility of a femoral stem in the A/P plane 10, the femoral head center 42 of the select femoral stem prosthesis template 40 (in the A/P plane or view) is aligned with the reference template femoral head center 18. Next, the longitudinal alignment axis 44 of the prosthesis template 40 is aligned with the A/P alignment axis 16 of the A/P reference template 100.

Upon visual inspection of the superimposed reference template and prosthesis template, the select femoral stem can be said to meet the minimum range of motion requirements, for example as specified by ISO 21535, for the A/P plane if its profile or boundary 46, as represented by the prosthesis template, is contained within the schematic profile defined on the A/P reference template, i.e., as represented by the boundaries 12 (see FIG. 3).

In an analogous manner, in the M/L view (corresponding to the M/L plane) the prosthesis template 50 is superimposed onto the M/L reference template 200. In an aligning step (shown in FIG. 4) for determining compatibility of a femoral stem in the M/L plane 20, the femoral head center 52 of the select femoral stem prosthesis template 50 (in the M/L plan or view) is aligned with the reference template femoral head center 18. Next, the longitudinal alignment axis 54 of the prosthesis template 50 is aligned with the M/L alignment axis 26 of the M/L reference template 200.

Figure 5:
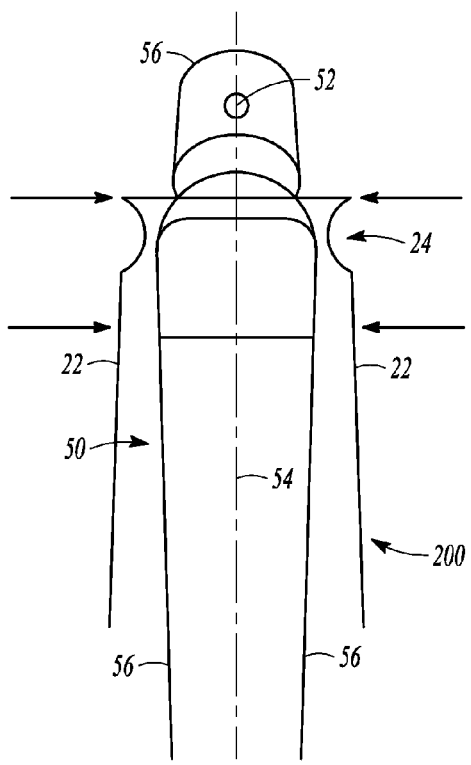
FIG. 5 illustrates visual inspection of the reference template of the present invention aligned with a prosthetic template in the M/L plane according to FIG. 4.

As indicated in FIG. 5, upon visual inspection, the femoral stem can be said to meet the minimum range of motion requirements, for example as specified by ISO 21535, for the M/L plane if its prosthesis template profile or boundary 56 is contained within the schematic profile defined on the M/L reference template 200, i.e., as represented by the boundaries 22 (see FIG. 5).

In an example, for a femoral head having a diameter of 28 mm, the virtual femoral stem and, thus, a compatible second prosthetic part, would have the following minimum articulation angles to meet the minimum range of motion requirement:

|  | Stem CCD<br>angle = 115° | Stem CCD<br>angle = 150° |
|---|---|---|
| Flexion/Extension | 103.8° | 107.4° |
| Abduction/Adduction | 75.5° | 75.5° |
| Inner and Outer Rotation | 110.2° | 214.2° |

Although the present invention has been described with reference to preferred embodiments, workers skilled in the art will recognize that changes may be made in form and detail without departing from the spirit and scope of the invention. The above Detailed Description includes references to the accompanying drawings, which form a part of the Detailed Description. The drawings show, by way of illustration, specific embodiments of present subject matter. These embodiments are also referred to herein as "examples." The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In the appended claims, the terms "including" and "in which" are used as the plain-English equivalents of the respective terms "comprising" and "wherein." The terms "including" and "comprising" are open-ended, that is, an article, system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction. Furthermore, while certain examples are shown and described with respect to a left or a right orientation, it is to be appreciated that the present disclosure is equally applicable to both left and right orientations unless, and only to the extent, otherwise specifically provided herein.

The Abstract is provided to allow the reader to quickly ascertain the nature of the technical disclosure. It is submitted with the understanding that it will not be used to interpret or limit the scope or meaning of the claims.

I claim:

1. A method for verifying compatibility between a first part and a second part of a joint prosthesis, with respect to at least one articulation parameter, the method comprising:

providing or receiving at least one two-dimensional reference template defining at least one verification plane and obtained on a basis of the first part, one or more constraints relating to the second part, and the at least one articulation parameter, the reference template comprising an alignment reference and one or more boundaries;

providing or receiving a two-dimensional prosthesis template corresponding to a shape of the second part, as viewed in the at least one verification plane;

aligning the prosthesis template with the at least one reference template by superimposing the two templates and aligning the prosthesis template to the reference template using the alignment reference; and considering the second part as compatible with the first part if the shape of the second part lies within the one or more boundaries of the at least one reference template, when the at least one reference template and the prosthesis template are aligned.

2. The method of claim 1, wherein the one or more boundaries of the reference template are obtained on the basis of a virtual second part having at least one predetermined geometrical property and fulfilling at least one predefined requirement for the articulation parameter for which the geometrical property is critical, including wherein the one or more boundaries of the reference template are obtained, at least in part, by a projection of the virtual second part into the at least one verification plane.

3. The method of claim 2, wherein the predetermined geometrical property of the second part is one of a diameter of the neck of a femoral stem, a fixation taper of the femoral stem, a CCD angle of the femoral stem, or an offset of a femoral head.

4. The method of claim 2, wherein the predefined requirement for the articulation parameter is a minimum articulation angle for a range of motion.

5. The method of claim 1, wherein the first part comprises an acetabular shell and a femoral head arrangement, the second part comprises a femoral stem to be fixed to the femoral head, and the articulation parameter comprises a range of motion with respect to articulation about at least one axis.

6. The method of claim 5, wherein the at least one axis comprises one of a first axis extending in an anterior-posterior direction or a second axis extending in a medial-lateral direction.

7. The method of claim 1, wherein the alignment reference comprises an articulation center and a straight alignment axis.

8. The method of claim 1, wherein the alignment reference comprises a head center of a femoral stem and a center line or neck axis of the femoral stem.

9. The method of claim 1, wherein the at least one reference template comprises a first and a second reference template, the at least one verification plane comprises a first and a second verification plane defining verification planes for, respectively, the first and second reference templates.

10. The method of claim 9, wherein the first verification plane is perpendicular to an anterior-posterior direction and the second verification plane is perpendicular to a medial-lateral direction.

11. A device for verifying compatibility between a first part and a second part of a joint prosthesis, comprising:

at least one two-dimensional reference template defining at least one verification plane and obtained on a basis of the first part, constraints relating to the second part, and an articulation parameter, the at least one reference template comprising a boundary and an alignment reference configured to align the at least one reference template with a two-dimensional prosthesis template having a shape of the second part, as viewed in the at least one verification plane.

12. The device of claim 11, wherein the boundaries of the at least one reference template are obtained on the basis of a virtual second part having at least one predetermined geometrical property and fulfilling at least one predefined requirement for the articulation parameter for which the geometrical property is critical.

13. The device of claim 11, wherein the alignment reference comprises an articulation center and a straight alignment axis.

14. The device of claim 11, wherein the first part comprises an acetabular shell and a femoral head arrangement, the second part comprises a femoral stem to be fixed to the femoral head, and the alignment reference comprises a head center of the femoral stem and a center line or neck axis of the femoral stem.

15. The device of claim 11, wherein the at least one reference template comprises a plurality of reference templates, each one of the plurality of reference templates represents a second part shape of a different size or scale.

16. The device of claim 15, wherein the scale is between 115% and 120% of an anatomical size of the first part.

17. The device of claim 11, further comprising a thin physical carrier, a transparency, or a piece of paper configured to receive and carry a marking or indicia, wherein the at least one reference template comprises the marking or indicia.

18. The device of claim 11, further comprising a computer system, including a visual display, and wherein the at least one reference template is adapted to be viewed on the display.

19. A method for producing a device for verifying compatibility between a first part and a second part of a joint prosthesis, with respect to at least one articulation parameter, the method comprising:
  providing or obtaining a two-dimensional reference template defining a verification plane, the reference template obtained on a basis of the first part, constraints relating to the second part, and to the articulation parameter; and
  providing or obtaining the reference template with one or more reference boundaries and an alignment reference for aligning the reference template with a two-dimensional prosthesis template having the shape of the second part as viewed in the first verification plane.

20. The method of claim 19, wherein the one or more boundaries of the reference template are obtained on the basis of a virtual second part having at least one predetermined geometrical property and fulfilling at least one predefined requirement for the articulation parameter for which the geometrical property is critical.

* * * * *

UNITED STATES PATENT AND TRADEMARK OFFICE
CERTIFICATE OF CORRECTION

PATENT NO. : 9,050,134 B2  
APPLICATION NO. : 13/799376  
DATED : June 9, 2015  
INVENTOR(S) : Rolf Meier Page 1 of 1

It is certified that error appears in the above-identified patent and that said Letters Patent is hereby corrected as shown below:

On the title page, item (54), in "Title", in column 1, line 2, delete "COMPATABILITY" and insert --COMPATIBILITY--, therefor On the title page, item (30), in "Foreign Application Priority Data", in column 1, line 1, delete "12194938" and insert --12194938.2--, therefor In the specification In column 1, line 2, delete "COMPATABILITY" and insert --COMPATIBILITY--, therefor Signed and Sealed this  
Twenty-seventh Day of October, 2015

Michelle K. Lee  
*Director of the United States Patent and Trademark Office*